United States Patent
Lee et al.

(10) Patent No.: US 9,844,780 B2
(45) Date of Patent: Dec. 19, 2017

(54) APPARATUS AND PLATFORM FOR DETECTION OF ALLERGEN

(71) Applicant: National Tsing Hua University, Hsinchu (TW)

(72) Inventors: Gwo-Bin Lee, Hsinchu (TW); Wen-Yen Huang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 15/063,028

(22) Filed: Mar. 7, 2016

(65) Prior Publication Data

US 2017/0014820 A1    Jan. 19, 2017

(30) Foreign Application Priority Data

Jul. 17, 2015    (TW) .............................. 104123315 A (51) Int. Cl.
*B01L 3/00*    (2006.01)
*G01N 33/53*    (2006.01)
*B01L 7/00*    (2006.01)

(52) U.S. Cl.
CPC ..... B01L 3/502715 (2013.01); B01L 3/50273 (2013.01); B01L 7/00 (2013.01); G01N 33/5308 (2013.01); *B01L 2200/025* (2013.01); *B01L 2200/04* (2013.01); *B01L 2200/0684* (2013.01); *B01L 2300/041* (2013.01); *B01L 2300/044* (2013.01); *B01L 2300/0819* (2013.01); *B01L 2300/0867* (2013.01); *B01L 2300/0874* (2013.01); *B01L 2300/0887* (2013.01); *B01L 2300/12* (2013.01); *B01L 2300/123* (2013.01); *B01L 2300/14* (2013.01); *B01L 2300/1827* (2013.01); *B01L 2400/0481* (2013.01); *B01L 2400/0487* (2013.01); *B01L 2400/0655* (2013.01)

(58) Field of Classification Search
CPC .... B01L 7/00; B01L 3/502715; B01L 3/5027; B01L 3/502; B01L 3/50; G01N 33/5308; G01N 33/53
USPC ......................................... 422/502, 500, 50
See application file for complete search history.

(56) References Cited

U.S. PATENT DOCUMENTS

2011/0044865 A1*  2/2011  Groisman ............... B01L 9/527
                                                           422/503

* cited by examiner

*Primary Examiner* — Christine T Mui
(74) *Attorney, Agent, or Firm* — WPAT, P.C., Intellectual Property Attorneys; Anthony King

(57) ABSTRACT

Provided is an allergen detecting apparatus that can combine with an allergen microarray chip, and the apparatus comprises a microfluidic chip and a clamping unit. The allergen microarray chip can be any commercial chip and a reaction region of the microfluidic chip is configured to fit tightly with a microarray region of the allergen microarray chip allowing a sample or a reagent to contact with a protein allergen disposed on the microarray region. The present invention also provides a platform comprising a control system configured to automatically perform the mixing/binding reactions of the antibody/antigen in the apparatus of the present invention to achieve a faster, more cost-effective, and accurate detection of allergens.

13 Claims, 6 Drawing Sheets

APPARATUS AND PLATFORM FOR DETECTION OF ALLERGEN

CROSS-REFERENCES TO RELATED APPLICATIONS

This application claims priority to Taiwan Priority Patent Application No. 104123315 filed on Jul. 17, 2015. All disclosure of which is incorporated herein by reference in its entirety.

BACKGROUND OF THE INVENTION

1. Field of the Invention

The present invention relates generally to an allergen detecting apparatus and a chip detecting platform, and more particularly, to provide an allergen detecting apparatus including a microfluidic chip and an allergen microarray chip, and a chip detecting platform applied therefrom.

2. The Prior Arts

Allergy refers to humoral or cellular inflammatory reactions of human immune system induced by allergens. It may generally make patients uncomfortable or cause tissue damages and even result in death when in a serious condition. The common allergic diseases in Taiwan including asthma, allergic rhinitis and hay fever, etc., and the allergens thereof may be proteins or small molecules of chemicals originated from environments, medicines, environmental microorganisms, food and so on. With the modernized development of society, the types of allergens are not only numerous but also have an increasing tendency. According to the data from World Allergy Organization, the number of allergy patients is about 30%-40% of the global population and it continues growing.

Currently, the major detection method of allergens is enzyme-linked immunosorbent assay (ELISA). However, before the test of ELISA, the sample needs to be heated and centrifuged such that allergens included therein will be denatured, loose antigenicity and reduce the solubility. These shortcomings affect the accuracy of measurement. Besides, the amount of reagents used by ELISA equipment is large, and the burden on the cost of detection for the patient is heavy. The newly emerging detection method is developed to utilize microarray chip, by which, different allergens are disposed on the surface of a substrate, and then the serum sample taken from the subject is mixed and reacted with the allergens. Since the detecting reactions of the microarray chip require manual operation and are complicate, it is not favorable for wider application and promotion for the allergen detection. As such, an automatic and high efficient allergen detection apparatus which can reduce the amount of the reagents used and the time taken is needed currently.

SUMMARY OF THE INVENTION

A primary objective of the present invention is to provide an allergen detecting apparatus for incorporating an allergen microarray chip having a microarray region. The allergen detecting apparatus comprises a microfluidic chip and a clamping unit. The microfluidic chip has an air control layer and a fluid channel layer, wherein the air control layer comprises at least an air control inlet, and the liquid channel layer comprises at least a liquid injection port and a reaction region. The clamping unit has a housing space for accommodating the microfluidic chip and at least a clamping member for fixing the microfluidic chip to allow the reaction zone to align and tightly fit with the microarray region. Besides, an area of the reaction region is not less than that of the microarray region. According to an embodiment of the present invention, the clamping unit comprises a cover and at least one clamping member, and the housing space is formed by the cover; the microfluidic chip further comprises a leakage-proof wall disposed in the fluid channel layer to prevent leakage when the microfluidic chip is incorporated with the allergen microarray chip.

Another objective of the present invention is to provide a chip detecting platform for detecting an allergen microarray chip. The chip detecting platform comprises an allergen detecting apparatus and a control system. The control system comprises an air control system and a temperature control system, and the control system is configured to automatically perform mixing and binding reactions of a sample or a reagent in the microfluidic chip with a protein allergen on the allergen microarray chip. According to an embodiment of the present invention, the air control system includes at least an air pressure source, and one or multiple electromagnetic pressure control valves. The temperature control system comprises at least a heat generator and a heat conduction member. Further, the sample is selected from the group consisting of blood, serums, plasma, urine, cerebrospinal fluids, tears, saliva, pharyngeal epithelial cells, sputum, lymph, dialysates, lavage fluids, fluids derived from organs or tissue cultures, and combinations thereof. In addition, the reagent is selected from the group consisting of secondary antibodies, buffers, and combinations thereof. According to another embodiment of the present invention, the chip detecting platform reduces the usage amount of the sample by at least 35%, reduces the usage amount of the reagent by at least 50%, and reduces the detection time by at least 50%.

Hereinafter, the present invention will be further illustrated with reference to the following examples. However, these examples are only provided for illustration purposes, but not to limit the scope of the present invention.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

The present invention provides an allergen detecting apparatus which can combine with the existing commercial allergen microarray chip. First, the allergen detecting apparatus according to the present invention comprises a microfluidic chip and a clamping unit, wherein the microfluidic chip has an air control layer and a fluid channel layer, and the clamping unit can fix the microfluidic chip to allow the reaction zone align and tightly fit with the microarray region. As such, any commercially available allergen microarray chip can all be effectively utilized to detect allergens rapidly and precisely. Secondly, the allergen detecting apparatus according to the present invention further connects with a control system whereby the detection procedures, for example the mixing and binding reactions of a sample or a reagent, and the reaction temperature, are automatically conducted and regulated. Consequently, the usage amount of the sample/reagent and detecting time are significantly reduced.

Definition

The terms of "microfluidic chip" and "chip" are exchangeable in the present specification, which indicates an independent integrated unit having a microfluidic reactor, one or more microfluidic channels, and one or more valves. The microfluidic chip also encompasses typical elements, such as pumps, chambers, mixers, and the like. In general, the microfluidic chip is made of elastomer, glass or silicon. Typically, the microfluidic chip is a box having height less than the length and the width thereof. Therefore, the shape of chip can be, but not limited to, cube or cylinder.

The term of "antibody" in the present specification indicates but not limited to a polypeptide or a fragment of a polypeptide substantially originated from an immunoglobulin, which can specifically recognize and bind to the object to be tested (i.e., antigen).

The term of "sample" in the present specification indicates the specimens collected from patients. The sample comprises but not limited to body fluids, such as blood, serums, plasma, urine, saliva, tears, pharyngeal epithelial cells, cerebrospinal fluids, lymph, dialysates, lavage fluids, and fluids derived from cells or tissues. The term of "sample" also indicates cells and ones derived therefrom, including cells in culture, the supernatant of the cell culture, and cell debris. In addition, the term of "sample" indicates the fluids derived from organs and tissue cultures, tissue biopsies, tumor biopsies, fecal sample, fluids extracted from tissues and cells isolated from solid tissues, tissue sections, and cell lysates. Particularly, the term of "sample" includes the one been treated after collection, for example treating and dissolving with reagents to make them be rich in components like polynucleotides or peptides, and fractions of samples from patients. Samples collected from patients can be used for diagnosis or monitoring. Further, the sample can be collected from mankind or other mammals.

EXAMPLE 1

Design of Integral Microfluidic Chip

Figure 1:
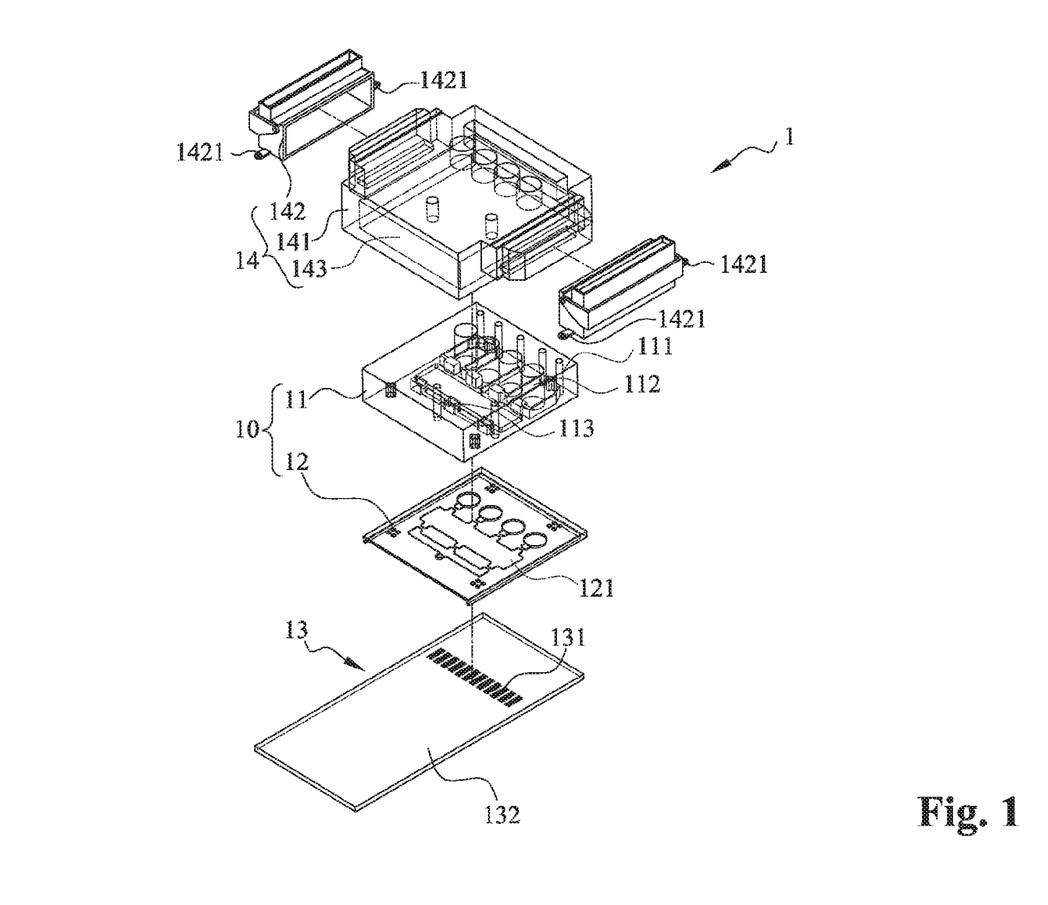
FIG. 1 is an exploded view of an allergen detecting apparatus according to an embodiment of the present invention.

Referring to FIG. 1, there is shown an allergen detecting apparatus 1 according to an embodiment of the present invention. The allergen detecting apparatus 1 is used to combine with an allergen microarray chip 13 which is commercially available. Generally, the commercial microarray chip for detecting allergens comprises a microarray region 131 deposited on a substrate 132, and at least an allergen protein is included on the microarray region 131. The allergen detecting apparatus 1 according to the present invention comprises a microfluidic chip 10 and a clamping unit 14, wherein the microfluidic chip 10 has an air control layer 11 and a fluid channel layer 12, and the clamping unit 14 has a cover 141 and a clamping member 142 having a fixing part 1421 for fastening the clamping member 142 on a platform.

Figure 2:
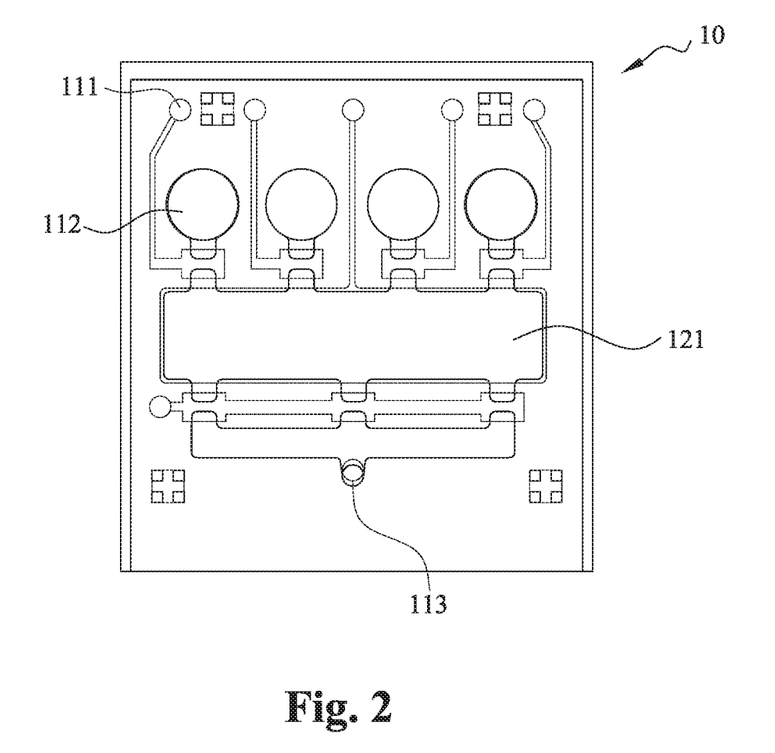
FIG. 2 is a top plan view showing the combination of an air control layer and a fluid channel layer of the microfluidic chip according to an embodiment of the present invention.

As seen from FIG. 1 and FIG. 2, the microfluidic chip 10 has an air control layer 11 and a fluid channel layer 12 disposed therebelow. Preferably, the air control layer 11 includes at least an air control inlet 111 for controlling air importing/removing from the air control layer 11 whereby the pressure difference is formed such that the fluid channel layer 12 becomes elastic deforming and pushes the fluids to flow. The fluid channel layer 12 includes at least a liquid injection port 112 and a reaction region 121. The sample and at least a reagent can be simultaneously or non-simultaneously injected through the opening of the air control layer 11 corresponding to the liquid injection port 112 to the reaction region 121. In addition, the fluid channel layer 12 includes a waste outlet 113 for removing the redundant solution or reacted solution by cooperating with the air control layer 11.

Figure 3:
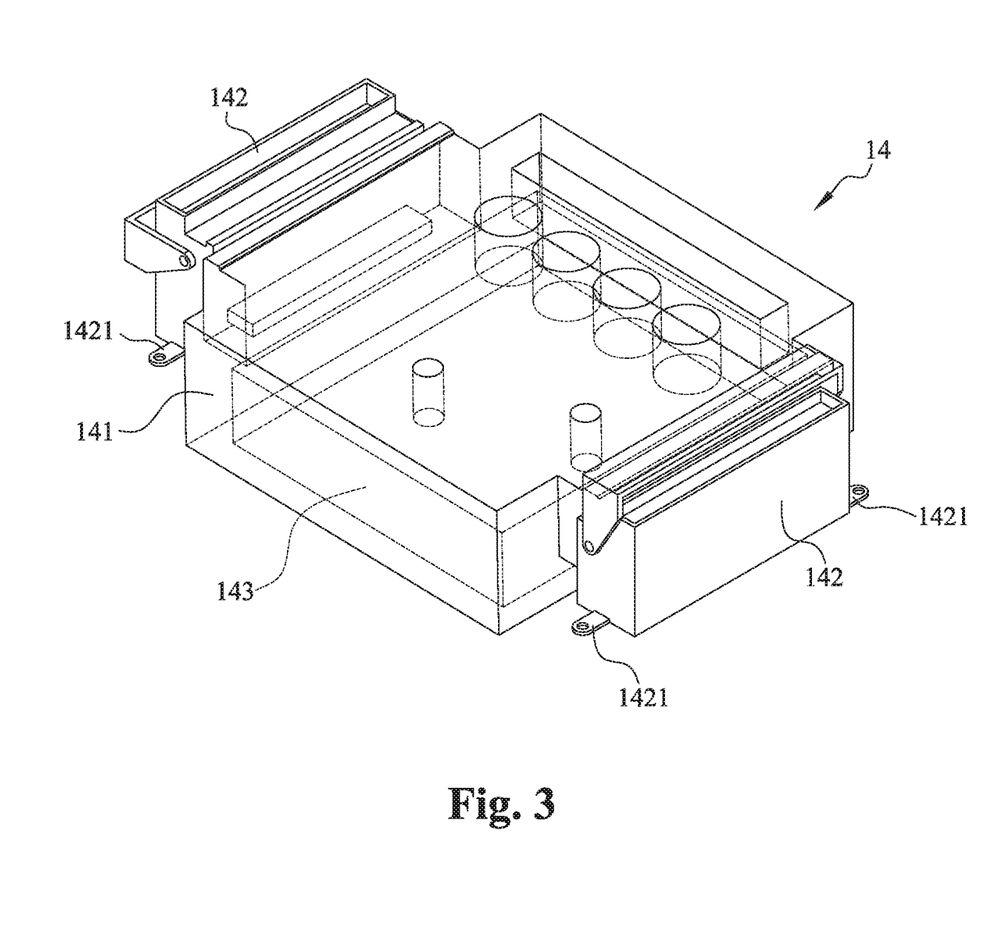
FIG. 3 is perspective view of a clamping unit of the allergen detecting apparatus according to an embodiment of the present invention.

As shown in FIG. 3, the clamping unit 14 includes a cover 141 and at least a clamping member 142. A housing space 143, accommodating the microfluidic chip 10, is formed by the cover 141; the cover 141 has an opening corresponding to the air control inlet 111 and the liquid injection port 112. The clamping member 142 is preferably rotatable or removable, and preferably disposed on two sides of the cover 141. The clamping member 142 further comprises at least a fixing part 1421 for fastening the clamping member 142 on a platform. Since the air control layer 11 and the fluid channel layer 12 of the microfluidic chip 10 may be an elastic material made of a high molecular polymer such as polydimethylsiloxane (PDMS), and the cover 141 of the clamping unit 14 may be a solid material made of plastics or glasses, the reaction region 121 of the microfluidic chip 10 can align precisely and closely fit with the microarray region 131 of the microarray chip 13 disposed therebelow.

Figure 4:
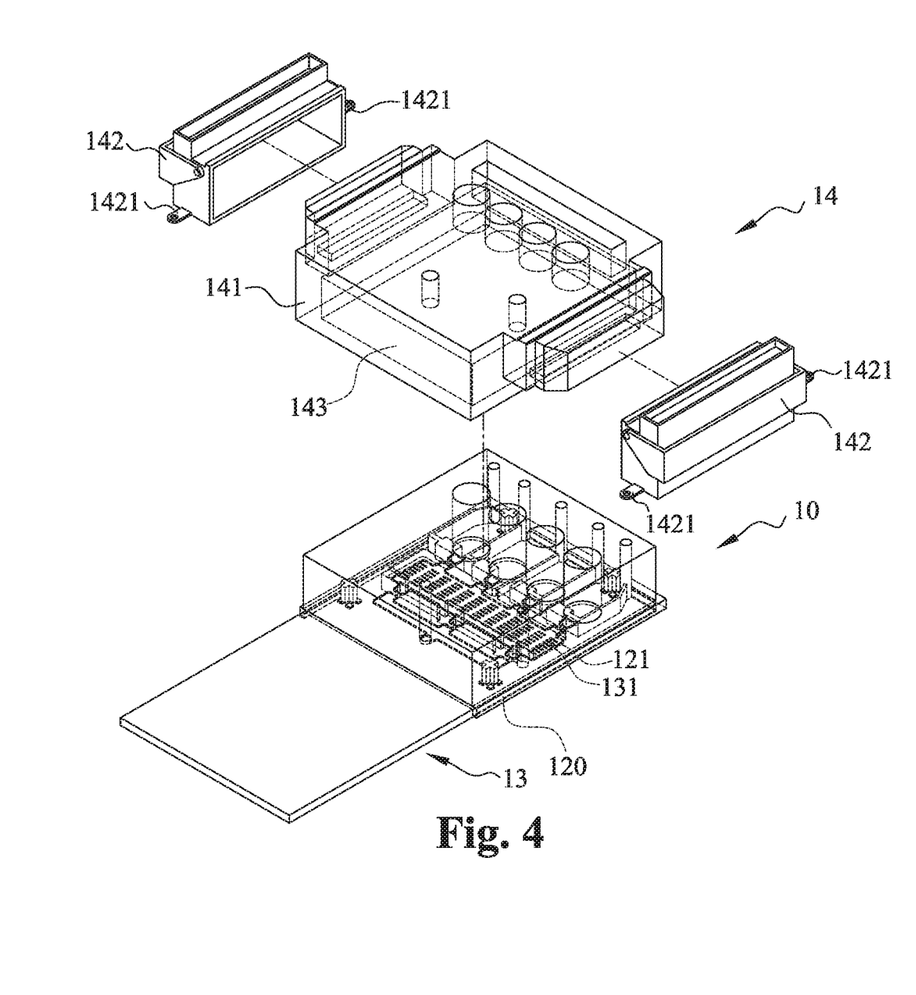
FIG. 4 is an exploded view of the clamping unit incorporated with the microfluidic chip and the allergen microarray chip according to an embodiment of the present invention.

Furthermore, the area of the reaction region 121 is not less than that of the microarray region 131. As shown in FIG. 4, when operating the allergen detecting apparatus 1 according to the present invention, the clamping unit 14 is combined with the microfluidic chip 10 from top to bottom. Therefore, the housing space 143 preferably has a length, a width and a height longer than that of the microfluidic chip 10. The two sides of the cover 141 of the clamping unit 14 preferably have protrusions respectively, and the clamping member 142 preferably has corresponding recesses so as to engage each other. The clamping member 142 further comprises at least a fixing part 1421 for fastening the clamping member 142 on a platform. The microfluidic chip 10 is received inside the housing space 143 of the clamping unit 14, and the cover 141 and the microfluidic chip 10 are held by the clamping member 142 whereby the reaction region 121 of the microfluidic chip 10 can align precisely and fit closely with the microarray region 131 of the microarray chip 13 disposed therebelow such that the sample or reagents injected into the microfluidic chip 10 can contact with at least an allergen protein on the microarray region 131. Therefore, the allergen detecting apparatus according to the present invention can directly utilize the existing commercial microarray chip without limitation to any materials, sizes or the types of allergen protein.

Figure 5:
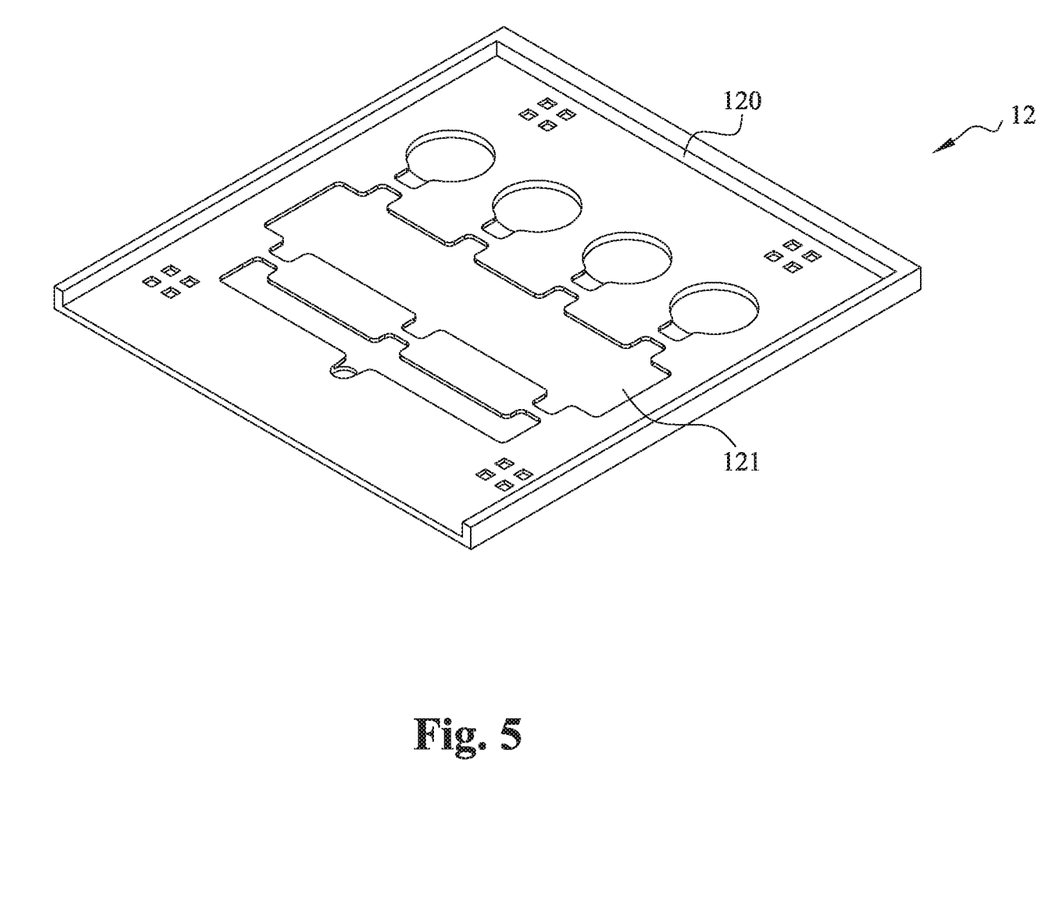
FIG. 5 is an schematic view of the fluid channel layer of the microfluidic chip seen from the down side according to an embodiment of the present invention.

In another aspect, in order to make the microfluidic chip 10 tightly fitted with the allergen microarray chip 13 to prevent leakage of the sample and the reagents from the fluid channel layer 12, a leakage preventing wall 120 is set on at least an edge of the fluid channel layer 12 as seen from FIG. 5. When operating, the elastic fluid channel layer 12 combines with the allergen microarray chip 13 downwardly, namely the leakage preventing wall 120 faces down. Referring to FIG. 4, the leakage preventing wall 120 can encase the hard allergen microarray chip 13. Preferably, the height of leakage preventing wall 120 is slightly higher than the thickness of the allergen microarray chip 13, and more preferably, the height is about 1 mm.

EXAMPLE 2

Automatic Allergen Detecting System

Figure 6:
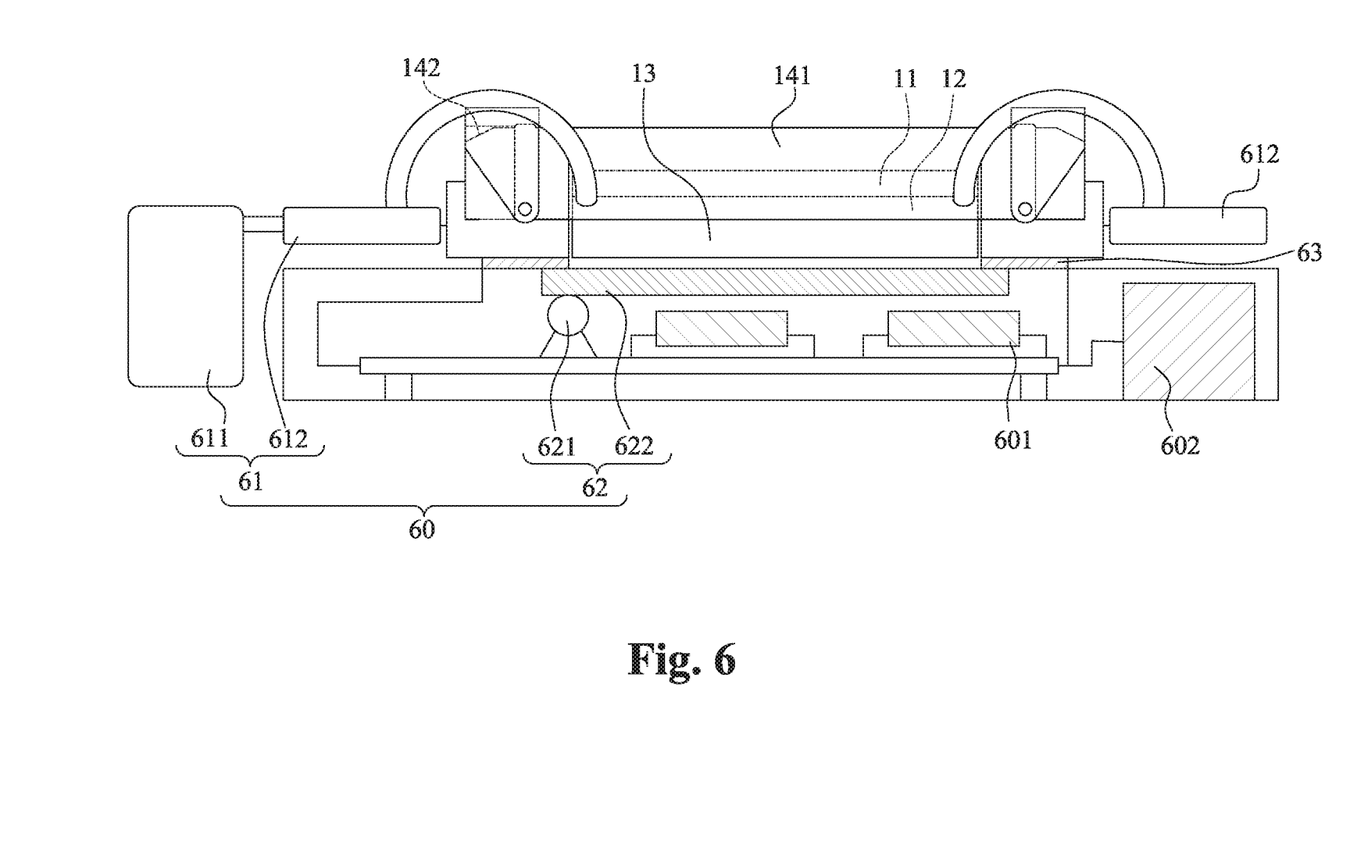
FIG. 6 is a schematic representation of automatic operation of the allergen detecting apparatus configured with a control system.

The allergen detecting apparatus 1 according to the present invention can further integrate with a control system such that the automatic detection of allergens is achieved. Referring to FIG. 6, the control system 60 comprises an air control system 61 and a temperature control system 62. When detecting the allergens, the control system 60 can automatically regulate the air control system 61 and the temperature control system 62 by a control circuit 601 electrically connected with a power supply 602. The air control system 61 which connects with the microfluidic chip 10 includes at least an air pressure source 611 and one or multiple electromagnetic pressure control valves 612. The electric current generated by the power supply 602 flows through the control circuit 601 to the electromagnetic pressure control valves 612 so as to open or close the same and results in the changes of the air pressure in the air control layer 11 of the microfluidic chip 10. Consequently, the fluid channel layer 12 deforms and makes the fluids flow. On the other hand, the temperature control system 62 includes at least a heat generator 621 and a heat conduction member 622 and which can also be regulated by the control circuit 601. The heat generator 621 can be any instruments generating stable heat source, and the heat conduction member 622 can be any materials with good thermal conductivity. Preferably, the size of the heat conduction member 622 is larger than that of the reaction region 121 and the microarray region 131.

In another aspect according the present invention, as shown in FIG. 6, the clamping member 142 is preferably rotatable or removable and preferably disposed on two sides of the cover 141. When the clamping unit 14 is employed in the allergen detection apparatus according to the present invention, the clamping member 142 is set on multiple thermos-insulation stands 63. The thermos-insulation stands 63 can be adjusted to appropriate height, for example to adjust it higher or lower to make the allergen microarray chip 13 be away from or close to the heat control member 622, so as to achieve accurate temperature controlling.

By integrating with the control system, the allergen detection apparatus according to the present invention can automatically perform the mixing/binding reactions of antibodies/antigens. First, following reactants was prepared: 130 µl each of serum sample (the concentration ratio is 1:9), the first wash buffer, the second wash buffer, the secondary antibody solution (the concentration ratio is 1:1500), and reverse osmosis water (RO), and then which were added to the microarray chip through the liquid injection port. Subsequently, there's no need of manual operation, and the allergen detection apparatus according to the present invention can automatically perform the mixing and binding reactions in the reaction region by way of the control system. For example, the serum sample can first be injected into the reaction region for 20 seconds, drawn for 20 seconds, and repeated for 30 cycles (20 minutes totally), and then washed with wash buffers for 3 times, namely the first wash buffer and the second buffer was respectively injected for 10 seconds, drawn for 5 seconds, and repeated for 4 cycles (1 minute totally). Subsequently, the secondary antibody solution was injected into the reaction region for 20 seconds, drawn for 20 seconds, and repeated for 30 cycles (20 minutes totally), and then washed with wash buffers for 3 times as previously described. Finally, the RO water was injected to rinse for one time, namely the RO water was injected for 10 seconds, drawn for 5 seconds, and repeated for 4 cycles (1 minute totally). Preferably, the flow speed of the sample/reagent is 81.32±2.33 µl/sec.

As described above, by way of the allergen detection apparatus according to the present invention, the amount of sample/reagent needed is only 130 µl respectively in comparison with 200-300 µl needed in manual operation so that about 35-57% of sample/reagent can be saved. In addition, the reaction time needed of the present invention is 45 min in comparison with the 90 min needed in manual operation so that about 50% of reaction time can be saved. On the other hand, the CV value of the present invention is 20% which is significantly better than 30% of the manual operation. The CV value indicates the accuracy and is calculated by dividing the standard deviation by the average value originated from the fluorescent signals detected on the microarray of 3 points of the same protein allergens. The smaller the CV value, the more accuracy it represents. Accordingly, the allergen detection apparatus according to the present invention can precisely detect allergens and reduces the usage amount of the sample/reagent and the detection time as well.

In summary, the allergen detection apparatus according to the present invention can directly utilize various existing commercial microarray chips for allergens detection. By employing the clamping unit, the reaction region of the microfluidic chip can tightly fit with the microarray region having protein allergens of the allergen microarray chip so that the aim of faster and accurate detection of allergens is achieved. Further, the allergen detection apparatus according to the present invention is integrated with a control system so as to automatically perform the allergen detection and reduce the sample/reagent usage and detection time as well compared to conventional manual methods. Accordingly, instability generated by conventional manual methods can be avoided, and the detection cost can also be dramatically reduced. Therefore, the present invention can not only be applied to faster, accurate and more-effective detection for existing allergen microarray chips but also provides an effective usage of detection chips will be developed in the future.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An allergen detecting apparatus for incorporating an allergen microarray chip having a microarray region, comprising:

a microfluidic chip having an air control layer and a fluid channel layer, wherein the air control layer comprises at least an air control inlet, and the fluid channel layer comprises at least a liquid injection port and a reaction region; and a clamping unit having a housing space for accommodating the microfluidic chip, a cover comprising at least a side protrusion, and at least a clamping member for fixing the microfluidic chip to allow the reaction region to align and tightly fit with the microarray region, wherein the clamping member comprises a recess corresponding to the side protrusion and a swing buckle for clipping the side protrusion.

2. The allergen detecting apparatus according to claim 1, wherein an area of the reaction region is not less than that of the microarray region.

3. The allergen detecting apparatus according to claim 1, wherein the housing space is formed by the cover.

4. The allergen detecting apparatus according to claim 1, wherein the microfluidic chip further comprises a leakage-proof wall disposed in the fluid channel layer to prevent leakage when the microfluidic chip is incorporated with the allergen microarray chip.

5. The allergen detecting apparatus according to claim 1, wherein the microarray region comprises at least a protein allergen.

6. A chip detecting platform for detecting an allergen microarray chip, comprising:

an allergen detecting apparatus according to claim 1; and a control system comprising an air control system connected with an air control layer of a microfluidic chip of the allergen detecting apparatus and a temperature control system, wherein the control system is configured to automatically perform mixing and binding reactions of a sample or a reagent in the microfluidic chip with a protein allergen on the allergen microarray chip.

7. The chip detecting platform according to claim 6, wherein the air control system comprises at least an air pressure source and one or more electromagnetic pressure control valves.

8. The chip detecting platform according to claim 6, wherein the temperature control system comprises at least a heat generator and a heat conduction member.

9. The chip detecting platform according to claim 6, wherein the sample is selected from the group consisting of blood, serums, plasma, urine, cerebrospinal fluids, tears, saliva, pharyngeal epithelial cells, sputum, lymph, dialysates, lavage fluids, fluids derived from organs or tissue cultures, and combinations thereof.

10. The chip detecting platform according to claim 6, wherein the reagent is selected from the group consisting of secondary antibodies, buffers, and combinations thereof.

11. The chip detecting platform according to claim 6, wherein the chip detecting platform reduces the usage amount of the sample by at least 35%.

12. The chip detecting platform according to claim 6, wherein the chip detecting platform reduces the usage amount of the reagent by at least 50%.

13. The chip detecting platform according to claim 6, wherein the chip detecting platform reduces the detecting time by at least 50%.

* * * * *